United States Patent [19]

Solofo et al.

[11] Patent Number: 5,292,978
[45] Date of Patent: Mar. 8, 1994

[54] SELECTIVE CYCLOALKYLATION OF NAPHTHALENE ON ZEOLITES

[75] Inventors: Jonis Solofo, Montpellier; Patrice Moreau, Saint-Gely-du-Fesc; Patrick Geneste; Annie Finiels, both of Montpellier, all of France

[73] Assignee: Michelin Recherche et Technique, Friebourg, Switzerland

[21] Appl. No.: 656,152

[22] PCT Filed: Jul. 23, 1990

[86] PCT No.: PCT/CH90/00178
§ 371 Date: Mar. 21, 1991
§ 102(e) Date: Mar. 21, 1991

[87] PCT Pub. No.: WO91/01959
PCT Pub. Date: Feb. 21, 1991

[30] Foreign Application Priority Data

Jul. 26, 1989 [FR] France .................. 89 10322

[51] Int. Cl.$^5$ .................. C07C 2/00; C07C 2/64
[52] U.S. Cl. .................. 585/467; 585/400; 585/430; 585/446
[58] Field of Search ........... 585/400, 430, 446, 467

[56] References Cited

U.S. PATENT DOCUMENTS

| | | |
|---|---|---|
| 2,229,018 | 1/1941 | Smith et al. |
| 2,904,607 | 9/1959 | Mattox et al. |
| 3,513,108 | 5/1970 | Kerr ..................... 502/79 |
| 3,515,680 | 6/1970 | Flank ..................... 502/79 |
| 3,641,177 | 2/1972 | Eberly, Jr. et al. |
| 3,773,652 | 11/1973 | Dille et al. ............. 208/49 |
| 3,786,106 | 1/1974 | Zuech et al. |
| 5,118,896 | 6/1992 | Steigelmann et al. ...... 585/467 |

FOREIGN PATENT DOCUMENTS

| | | |
|---|---|---|
| 638756 | 4/1936 | Fed. Rep. of Germany . |
| 1934426 | 7/1970 | Fed. Rep. of Germany . |
| 2208363 | 10/1973 | Fed. Rep. of Germany . |

OTHER PUBLICATIONS

Chemical Abstracts, vol. 94, No. 3, Jan. 19, 1981, p. 403, 15325z.

Primary Examiner—Asok Pal
Assistant Examiner—P. Achutamurthy
Attorney, Agent, or Firm—Brumbaugh, Graves, Donohue & Raymond

[57] ABSTRACT

A method of cycloalkylating naphthalene with at least one cyclic group, characterized by the following points:
 a) as catalyst, there is used a zeolite of faujasite structure having pore openings greater than 6.7 Å, the silica/alumina ratio of this zeolite being greater than 2.5 and its residual content of alkaline ion(s) being less than 3%;
 b) the reaction is carried out batchwise in heterogenous liquid/solid phase at a temperature of between 20° C. and 250° C., under a pressure at most equal to 30 bars. Cycloalkylated naphthalenes are obtained by this method, in particular 2,6-dicyclohexyl naphthalene.

11 Claims, No Drawings

SELECTIVE CYCLOALKYLATION OF NAPHTHALENE ON ZEOLITES

The present invention relates to a method for the selective cycloalkylation of naphthalene using zeolites as catalyst. The invention concerns, in particular, a method of preparing monocycloalkylated aromatic compounds and a method of preparing dicycloalkylated aromatic compounds. The mono-and dicyclo-alkylated aromatic compounds are used in numerous fields, and it is important to prepare them selectively. Methods for the preparation of cycloalkylated aromatic compounds are known in the literature.

The production of aromatic compounds containing cycloalkyl groups using aluminum halides is known, for instance a synthesis of mono- or dicyclo-hexyl naphthalenes are with $AlCl_3$, such reactions being described in particular in the following publications:

D. Bodroux, Annales de Chimie 1929, (10) 11, 535;

Charles C. Price, J. Am. Chem. Soc., 1943, 65, 439;

E. S. Pokrovskaya, J. Gen. Chem (USSR), 1939, 9, 1953.

This method leads to a low yield and an absence of selectivity and, furthermore, it is not economical.

The patents or patent applications DE-C-638 756, DE-A-2 208 363, U.S. Pat. No. 2,229,018, and U.S. Pat. No. 3,786,106 describe the alkylation of aromatic compounds by olefins, for instance cyclic olefins, in the presence of catalysts which are clays, for instance montmorillonite, kaolin, hydrosilicates, and bleaching earths. These methods are not selective.

U.S. Pat. No. 2,904,607, U.S. Pat. No. 3,641,177, U.S. Pat. No. 4,393,262, DE-A 3 334 084, EP-A-280 055, and J. Catal. 1986, 101, p. 273 describe the alkylation of aromatic products using zeolites as catalysts with linear alkylation agents such as, for instance, olefins having 2 to 4 carbon atoms, or methanol. These documents do not describe the alkylation of aromatic products with cyclic alkyl groups.

Patent Application DE-A-1 934 426 describes the continuous method of preparing alkylated aromatic compounds. This document cites numerous catalysts of zeolite type, for instance nature zeolites such as gmelinite, dachiardite, faujasite, heulandite and mordenite, or synthetic zeolites such as the omega, L and Y zeolites. This document also cites numerous aromatic compounds and a large variety of alkylation agents. This method is carried out in two steps. In the first step, the alkylation is effected with an alkylation agent in the presence of zeolites suspended in the liquid medium. The alkylation is not selective and a mixture of mono and polyalkyl aromatics is obtained. In order to remedy this lack of selectivity, the reaction mixture coming from the first step is contacted in a second step with a zeolite, without there being a suspension and without alkylating agent, so as to effect a transalkylation. Despite this second step, the overall selectivity at the end of these two steps remains low.

The object of the present invention is to provide a method for the cycloalkylation of naphthalene with an alkylating agent, using at least one zeolite as catalyst, the method being characterized surprisingly by both a high rate of conversion and a substantial selectivity, while using a larger ratio of alkylating agent to aromatic compound than used in general in the prior art. This method is characterized by the following points:

a) as catalyst, there is used at least one zeolite of faujasite structure having pore openings larger than 6.7 Å, the silica/alumina ratio of this zeolite being greater than 2.5 and its residual content of alkaline ion(s) being less than 3%;

b) the reaction is carried out batchwise in heterogenous liquid/solid phase at a temperature between 20° C. and 250° under a pressure of at most 30 bars, the zeolite or zeolites being suspended in the reaction medium;

c) the molar ratio of alkylating agent to naphthalene is at least equal to 1.

The cycloalkyls fixed by reaction on the naphthalene are for instance cyclopentyl or cyclohexyl, these alkyls possibly having substituents. The alkylation reagents must have at least one double bond or a reactive group, for instance a halogen or an OH group, such reagents being, for instance, cyclohexene, chloro- or bromo-cyclohexane or cyclohexanol.

The zeolites used in the method of the invention may be in protonic form or cations exchanged, in particular rare earth cations (for example La, Ce, Pr, Gd, Yb).

The method of the invention is particularly adapted to the cycloalkylation of naphthalene in order to obtain 2,6-dicyclohexyl naphthalene, the alkylation reagent being for instance chlorocyclohexane or bromocyclohexane.

The invention also concerns the aromatic compounds obtained by the method described above, in particular 2,6-dicyclohexyl naphthalene. This product is very important in polymer chemistry, since it makes it possible by oxidation to obtain compounds containing hydroxyl or carboxyl groups in 2,6 position, which products serve in particular for the synthesis of aromatic polyamides or polyesters.

The invention will be readily understood on basis of the following non-limitative examples.

In these examples, there are used zeolites Y of faujasite structure, zeolites of mordenite structure and zeolites of omega structure, all of these zeolites being in their protonic form. These zeolites are the following:

an HY zeolite, hereinafter referred to as "HY1", marketed by Union Carbide in the form $NH_4Y$, under the name of Linde SK 41;

an HY zeolite, hereinafter referred to as "HY2", marketed by Chemische Fabrik Uetikon in HY form under the name Z6-03-02;

an US-HY zeolite which is an ultra-stable zeolite obtained by treating the zeolite HY2 by the method described by J. Scherzer and J. L. Bass in J. Catal, 1973, 28, 101; this US-HY zeolite having a residual content of alkaline ion(s) of less than 1%;

a zeolite of mordenite structure, hereinafter designated "MOR 1", marketed by the Norton Company under the name Zeolon 100 H;

a zeolite of mordenite structure, hereinafter designated "MOR 2", obtained from the zeolite MOR 1 by treatment with 1N hydrochloric acid for 3 hours at 70° C.;

a zeolite of omega structure, hereinafter designated "OMEGA", prepared in accordance with French Patent Application 85-07772 and activated by the method described in J. Catal. 111, 94-105 (1988).

Before each reaction, the zeolites undergo a thermal calcination treatment in a stream of air of 200 cc per minute. The calcination is effected in accordance with one of the following two methods:

calcination for 6 hours at 300° C. (zeolites US-HY, HY1 and HY2);

calcination for 6 hours at 500° C. (for the other zeolites).

This calcination is effected in an oven which permits a linear rise of the temperature of 50° C. per hour, starting from room temperature, the time of increase of the temperature being added to the previously indicated calcination times.

The characteristics of the calcinated zeolites ready for use are given in the following Table I:

TABLE I

| Characteristics (Powder) | | | |
|---|---|---|---|
| Zeolite | % $Na_2O$ (% by wt.) | % $Al_2O_3$ (% by wt.) | % $SiO_2$ (% by wt.) |
| HY1 | 2.5 | 22.3 | 64.9 |
| HY2 | 2.5 | 23.5 | 72.5 |
| US-HY | <0.2 | 25 | 75 |
| MOR1 | 0.4 | 9 | 72 |
| MOR2 | 0.01 | 7.1 | 92.8 |
| OMEGA | 0.3 | 22.1 | 66.3 |

| Zeolite | $\frac{SiO_2}{Al_2O_3}$ (weight) | Specific surface ($m^2/g$) | Opening of the pores (Å) |
|---|---|---|---|
| HY1 | 2.9 | 948 | 7.4 |
| HY2 | 3.0 | 700 | 7.4 |
| US-HY | 3.0 | 675 | 7.4 |
| MOR1 | 8.0 | 550 | 6.7 × 7.0 |
| MOR2 | 13.0 | 510 | 6.7 × 7.0 |
| OMEGA | 3.0 | 140 | 8 |

Unless otherwise indicated, all the alkylation tests described in the following examples are carried out in a 100-ml autoclave of the BURTON-CORBLIN Company, provided with an internal rotary agitator with magnetic drive, a sampling valve, a pressure gauge and an apparatus for measuring the speed of rotation. The autoclave is heated by an oven the regulation of the temperature of which is effected by a regulator manufactured by the SOTELEM Company.

The analyses are carried out with a DELSI series 330 chromatograph provided with an OVI capillary column of 25 m having a flame ionization detector. It is coupled to a DELSI ENICA 21 integrator. For each test, the reaction medium is analyzed at least twice. Nitrobenzene is used as internal standard and it is added again to the samples serving for the analysis.

The conditions of chromatographic analysis are as follows:
  temperature of the injector: 330° C.;
  temperature of the detector: 320° C.;
  programming of the temperature of the oven: adapted to the compounds, for instance for naphthalene: heating from 100° C. to 280° C., the rate of heating being 15° C./min;
  pressure of the hydrogen serving as vector gas: 0.65 bar.

The determination of the structure of the products of the reaction is effected by a unit consisting of a gas chromatograph coupled with a mass spectrometer. The chromatograph is equipped with a capillary column of type OVI of 25 m.

The conditions of analysis with this unit are as follows:
  temperature of the injector: 250° C.;
  temperature of the detector: 250° C.;
  programming of the temperature of the oven: adapted to the compounds, for instance for naphthalene: heating from 100° C. to 280° C., with a rise in temperature of 10° C./min;
  pressure of the helium used as vector gas: 0.5 bar.

Example 1

The purpose of this example is to compare the results obtained with the zeolites described above upon the cyclohexylation of naphthalene, using bromocyclohexane as alkylating agent and cyclohexane as solvent.

For each zeolite, the reaction is carried out in the following manner:

50 cc of cyclohexane, 1 g of calcined powdered zeolite and 1.62 g of bromocyclohexane (10 mmols) are introduced into the autoclave. The autoclave is closed and agitated at 680 rpm to obtain a suspension of the catalyst in the reaction medium, while heating in such a manner that the temperature of the reaction medium increases from 25° C. to 200° C. in 10 minutes. The autogenous pressure is then 15 bars within the autoclave. Samples of the reaction are then taken for analysis in the case of tests 1 to 4, and the autoclave cooled. In the case of tests 5 and 6, the samples are taken 70 minutes after the start of the agitation and the heating, the temperature of the autoclave being maintained at 200° C. for 60 minutes before these samplings, the pressure remaining equal to 15 bars. In all cases, after cooling, the reaction medium is filtered in order to remove the zeolite powder, which is washed with 50 ml of ether. This wash ether is added to the filtrate in order to obtain an organic phase of which samples are taken in order to effect an analysis which coincides with the analysis of the last sampling effected.

The results of the tests are set forth in Table II. In this Table II, as in the other tables which follow, the total conversion is expressed in molar %. In general, there is understood by total conversion (conversion rate) the molar ratio:

$$\frac{\text{number of mols of cycloalkylated naphthalenes}}{\text{number of mols of initial naphthalene}}$$

and the distribution of the products is expressed in molar %, as is the ratio of the products:

TABLE II

| | Test No. | | |
|---|---|---|---|
| | 1 | 2 | 3 |
| Reaction conditions | | | |
| Final temperature °C. | 200 | 200 | 200 |
| Reaction time (minutes) | 10 | 10 | 10 |
| Molar ratio: | | | |
| alkylating agent naphthalene | 2 | 2 | 2 |
| catalyst | HY1 | HY2 | US-HY |
| Total conversion | 83 | 96 | 96 |
| Distribution of the products | | | |
| Monoalkylated | 71 | 65 | 31 |
| Dialkylated | 16 | 31 | 67 |
| Others | 13 | 4 | 2 |
| Ratio of the products | | | |
| 2-monocyclohexyl naphthalene monocyclohexyl naphthalenes | 46 | 18 | 6 |
| 2,6-dicyclohexyl naphthalene dicyclohexyl naphthalenes | 11 | 33 | 43 |
| 2,6-dicyclohexyl + 2,7-dicyclohexyl naphthalenes dicyclohexylnaphthalenes | 25 | 65 | 82 |

| | Test No. | | |
|---|---|---|---|
| | 4 | 5 | 6 |
| Reaction conditions | | | |
| Final temperature °C. | 200 | 200 | 200 |
| Reaction time (minutes) | 10 | 70 | 70 |
| Molar ratio: | | | |

TABLE II-continued

| alkylating agent naphthalene | 2 | 2 | 2 |
|---|---|---|---|
| catalyst | MOR1 | MOR2 | OMEGA |
| Total conversion | <1 | 6 | 0 |
| Distribution of the products | | | |
| Monoalkylated | — | 56 | — |
| Dialkylated | — | 44 | — |
| Others | — | — | — |
| Ratio of the products | | | |
| 2-monocyclohexyl naphthalene monocyclohexyl naphthalenes | — | 46 | — |
| 2,6-dicyclohexyl nahpthalene dicyclohexyl naphthalenes | — | 16 | — |
| 2,6-dicyclohexyl + 2,7-dicyclohexyl naphthalenes dicyclohexylnaphthalenes | — | 27 | — |

Tests 1 to 3 with the zeolites HY1, HY2, US-HY are in accordance with the invention, while Tests 4 to 6 with the zeolites MOR1, MOR2, and OMEGA are not in accordance with the invention.

From Table II it is noted that the method of the invention unexpectedly makes it possible to obtain all of the following advantages:

the overall conversion rate is very high (from 83 to 96%), while the zeolites MOR1, MOR2 and OMEGA lead to very low or zero conversion rates (from 0 to 6%);

the selectivity is great; in fact the zeolites HY1 and HY2 lead to a strong proportion of monocyclohexyl naphthalenes (71% and 65%), while the zeolite US-HY leads to a strong proportion of dicyclohexyl naphthalenes (67%).

The zeolite US-HY is particularly interesting with respect to selectivity, since it leads not only to a predominant dicyclohexylation but also to a high selectivity in 2,6+2,7 isomers (82%) with respect to all of the dicyclohexyl naphthalenes. The HY2 and US-HY catalysts furthermore have the advantage of leading to very low percentages of tri- and tetra-substituted naphthalenes.

This substantial conversion and this substantial selectivity are obtained with a high ratio of alkylating agent to naphthalene, which is very advantageous from an economic standpoint.

EXAMPLE 2

This example is carried out in a manner similar to Example 1 with the zeolites HY1 and US-HY, with the difference that an open reactor at atmospheric pressure is used instead of an autoclave, using for each test 20 mmols of bromocyclohexane and carrying out the reaction for 6 hours at 80° C. The zeolite powder is added to the naphthalene/cyclohexane mixture which has been previously heated to 80° C. before addition of the bromocyclohexane.

The results of the tests are given in Table III.

TABLE III

| | Test No. | |
|---|---|---|
| | 7 | 8 |
| Reaction conditions | | |
| Temperature °C. | 80 | 80 |
| Reaction time (minutes) | 360 | 360 |
| Alkylation agent | Bromocyclohexane | |
| Molar ratio: | | |
| alkylating agent naphthalene | 4 | 4 |
| catalyst | HY1 | US-HY |
| Total conversion | 57 | 84 |
| Distribution of the products | | |
| Monocyclohexylnaphthalenes | 96 | 90 |
| Dicyclohexylnaphthalenes | 4 | 10 |
| Ratio of the products | | |
| 2-Cyclohexyl naphthalene monocyclohexylnaphthalenes | 60 | 38 |

An examination of Table III again shows that the method in accordance with the invention permits a high total conversion rate with the two zeolites, but the reaction being directed here towards monocyclohexylation as a result of the low temperature. The zeolite US-HY permits a higher overall conversion rate than that obtained with the zeolite HY1 (84% for US-HY, 50% for HY1), the selectivity in monocyclohexylnaphthalenes being of the same order for both zeolites.

EXAMPLE 3

This example is carried out by alkylating naphthalene, varying the alkylation agent, with the zeolites US-HY, HY1, HY2. The alkylation agents used are the following: bromocyclohexane (BCH), chlorocyclohexane (CCH), bromocyclopentane (BCP), cyclohexanol (CHL), benzyl chloride (CBZ).

The test conditions are as follows:

quantities used 0.64 g of naphthalene (5 mmols), 50 cc of cyclohexane, 1.0 g of zeolite, 10 mmols of alkylation agent, agitation of the reactor: 680 rpm, starting of the reactor at room temperature, analysis of the reaction products effected when the temperature of the reaction medium reaches 200° C., that is to say 10 minutes after the starting of the reactor and therefore after the start of the heating, the autogenous pressure in the reactor then being 15 bars.

The results are given in Table IV below.

TABLE IV

| | Test No. | | |
|---|---|---|---|
| | 9 | 10 | 11 |
| Reaction conditions | | | |
| Final temperature °C. | 200 | 200 | 200 |
| Reaction time (minutes) | 10 | 10 | 10 |
| Alkylation agent | BCH | BCH | BCH |
| Molar ratio: | | | |
| alkylating agent: naphthalene | 2 | 2 | 2 |
| catalyst | US-HY | HY2 | HY1 |
| Total conversion | 96 | 96 | 83 |
| Distribution of the products | | | |
| Monoalkylated | 31 | 65 | 71 |
| Dialkylated | 67 | 31 | 16 |
| Trialkylated | — | — | — |
| Others | 2 | 4 | 13 |
| Ratio of the products: | | | |
| 2-monoalkyl naphthalene monoalkyl naphthalenes | 6 | 18 | 46 |
| 2,6-dialkyl naphthalenes dialkyl naphthalenes | 43 | 33 | 11 |
| 2,6-dialkyl + 2,7-dialkyl naphthalenes dialkyl naphthalenes | 82 | 65 | 25 |

| | Test No. | | |
|---|---|---|---|
| | 12 | 13 | 14 |
| Reaction conditions | | | |
| Final temperature °C. | 200 | 200 | 200 |
| Reaction time (minutes) | 10 | 10 | 10 |

TABLE IV-continued

| Alkylation agent | CCH | CCH | CCH |
|---|---|---|---|
| Molar ratio: | | | |
| alkylating agent naphthalene | 2 | 2 | 2 |
| catalyst | US-HY | HY2 | HY1 |
| Total conversion | 97 | 89 | 78 |
| Distribution of the products | | | |
| Monoalkylated | 62 | 76 | 72 |
| Dialkylated | 38 | 24 | 11 |
| Trialkylated | — | — | — |
| Others | — | — | 17 |
| Ratio of the products | | | |
| 2-monoalkyl naphthalene monoalkyl naphthalenes | 22 | 41 | 46 |
| 2,6-dialkyl naphthalenes dialkyl naphthalenes | 38 | 21 | 21 |
| 2,6-dialkyl + 2,7-dialkyl naphthalenes dialkyl naphthalenes | 59 | 37 | 35 |

| | Test No. | | |
|---|---|---|---|
| | 15 | 16 | 17 |
| Reaction conditions | | | |
| Final temperature °C. | 200 | 200 | 200 |
| Reaction time (minutes) | 10 | 10 | 10 |
| Alkylation agent | BCP | BCP | CHL |
| Molar ratio: | | | |
| alkylating agent naphthalene | 2 | 2 | 2 |
| catalyst | US-HY | HY2 | HY1 |
| Total conversion | 97 | 91 | 28 |
| Distribution of the products | | | |
| Monoalkylated | 25 | 50 | 75 |
| Dialkylated | 58 | 47 | 3 |
| Trialkylated | 3 | 2 | — |
| Others | 14 | 1 | 22 |
| Ratio of the products | | | |
| 2-monoalkyl naphthalene monoalkyl naphthalenes | 0 | 44 | 47 |
| 2,6-dialkyl naphthalenes dialkyl naphthalenes | 39 | 27 | 27 |
| 2,6-dialkyl + 2,7-dialkyl naphthalenes dialky naphthalenes | 84 | 47 | 41 |

| | Test No. |
|---|---|
| | 18 |
| Reaction conditions | |
| Final temperature °C. | 200 |
| Reaction time (minutes) | 10 |
| Alkylation agent | CBZ |
| Molar ratio: | |
| alkylating agent naphthalene | 2 |
| catalyst | US-HY |
| Total conversion | 12 |
| Distribution of the products | |
| Monoalkylated | 100 |
| Dialkylated | — |
| Trialkylated | — |
| Others | — |
| Ratio of the products | |
| 2-monoalkyl naphthalene monoalkyl naphthalenes | 80 |
| 2,6-dialkyl naphthalenes dialkyl naphthalenes | — |
| 2,6-dialkyl + 2,7-dialkyl naphthalenes dialkyl naphthalenes | — |

All the tests are in accordance with the invention except when the alkylation agent is benzyl chloride, which is not a cycloalkylation agent (CBZ test No. 18).

For all the tests in accordance with the invention except when the alkylation agent is cyclohexanol (CHL), the overall conversion rate is very high, the zeolite US-HY leading in each case to a better selectivity in dicycloalkylated products (67%, 38%, 58%) than the other zeolites, which are, however, selective for the obtaining of mono and/or dicycloalkylated products.

In the case of cyclohexanol, the total conversion is less although substantial.

The reaction with benzyl chloride (CBZ), which is not in accordance with the invention, leads on the other hand to a very low total conversion rate.

In the preceding examples in accordance with the invention, the various products obtained can be purified and separated by conventional methods, such as for instance vacuum distillation and crystallization.

The alkylation temperature is preferably at least equal to 50° C. and at most equal to 220° C. The temperature is preferably at least equal to 50° C. and at most equal to 140° C. if one desires essentially or entirely a monoalkylation and higher than 140° C. and at most equal to 220° C. if one desires essentially or entirely a dialkylation.

In the method in accordance with the invention, the conversion rate is preferably greater than 50% and it makes it possible to obtain more than 50% either of monocycloalkylnaphthalenes or of dicycloalkylnaphthalenes with respect to the total cycloalkylnaphthalenes obtained, these percentages being mol percentages. The conversion rate is advantageously greater than 80% and the method makes it possible to obtain more than 60% of either monocycloalkylnaphthalenes or of dicycloalkylnaphthalenes, in molar ratios, with respect to the total cycloalkylnaphthalenes obtained.

Of course, the invention is not limited to the embodiments which have been described above. Thus, for instance, the molar ratio of alkylation agent to naphthalene may vary within wide limits beyond 1.

What is claimed is:

1. A method for preparing a cycloalkyl naphthalene comprising forming a reaction mixture comprising naphthalene, a cycloalkylating agent and a solid catalyst, said catalyst being a zeolite of faujasite structure having pore openings of greater than 6.7 Å, a silica/alumina ratio of greater than 2.5 and a residual content of at least one alkaline ion of less than 3%; and reacting the naphthalene and the cycloalkylating agent at a temperature of between 20° C. and 250° C. and a pressure of at most 30 bars for a period of time sufficient to form cycloalkylnaphthalenic products, wherein the molar ratio of cycloalkylating agent to naphthalene is at least one.

2. A method according to claim 1, wherein the catalyst has a residual content of at least one alkaline ion of less than 1%.

3. A method according to claim 1 or 2, wherein the temperature is at least equal to 50° C. and at most equal to 220° C.

4. A method according to claim 1, wherein the cycloalkylating agent is a substituted cyclohexane.

5. A method according to claim 3 wherein the alkylation is essentially a monoalkylation.

6. A method according to claim 5 wherein the temperature is at least equal to 50° C. and at most equal to 140° C.

7. A method according to claim 3 wherein the alkylation is essentially a dialkylation.

8. A method according to claim 7 wherein the temperature is greater than 140° C. and at most equal to 220° C.

9. A method according to claim 1 wherein the reaction is carried out batchwise in heterogeneous liquid/solid phase and the catalyst is suspended in the reaction medium.

10. A method according to claim 1 wherein the cycloalkylating agent is a cyclohexylating agent.

11. A method for preparing 2,6-dicyclohexyl naphthalene comprising forming a reaction mixture comprising naphthalene, a cyclohexylating agent and a solid catalyst, said catalyst being a zeolite of faujasite structure having pore openings of greater than 6.7 Å, a silica/alumina ratio of greater than 2.5 and a residual content of at least one alkaline ion of less than 3%; and reacting the naphthalene and the cycloahexylating agent at a temperature of between 20° C. and 250° C. and a pressure of at most 30 bars for a period of time sufficient to form 2,6-dicyclohexyl napthalene, wherein the molar ratio of cyclohexylating agent to naphthalene is at least one.

* * * * *

UNITED STATES PATENT AND TRADEMARK OFFICE
CERTIFICATE OF CORRECTION

PATENT NO. : 5,292,978
DATED : March 8, 1994
INVENTOR(S) : Solofo et al.

It is certified that error appears in the above-indentified patent and that said Letters Patent is hereby corrected as shown below:

Col. 1, line 17, "a" should read --the--; between lines 60-61, insert --Summary of the Invention--. Col. 2, line 20, "cations exchanged" should read --exchanged by cations--; before line 35 insert --Detailed Description of Invention--; line 64, "cc" should read --cm$^3$--. Col. 3, line 36, "oven the" should read --oven, the--; line 44, delete "again"; line 39, "330" should read --330 gas phase--; lines 37-38, "manufactured by" should read --from--; line 57, "gas" should read --gas phase--. Col. 4, line 10, "50 cc" should read --0.64g of naphthalene (5mmols), 50 cm$^3$--; line 53, "Total Conversion" should be underlined. Col. 6, line 20, "50%" should read --57%--; line 31, "cc" should read --cm$^3$--; line 59, "2,6-dialkyl naphthalenes" should read --2,6-dialkyl naphthalene--. Col. 7, lines 14, 35 and 56, "2,6-dialkyl naphthalenes" should read --2,6-dialkyl naphthalene--. Col. 10, line 5, "cycloahexylating" should read --cyclohexylating--.

Signed and Sealed this

Fourth Day of April, 1995

Attest:

BRUCE LEHMAN

Attesting Officer

Commissioner of Patents and Trademarks